(12) United States Patent
Wiklof et al.

(10) Patent No.: US 7,476,197 B2
(45) Date of Patent: Jan. 13, 2009

(54) SCANNED BEAM IMAGERS AND ENDOSCOPES UTILIZING MULTIPLE LIGHT COLLECTORS

(75) Inventors: Christopher A. Wiklof, Everett, WA (US); Michael P. Weir, Blanchester, OH (US)

(73) Assignee: Microvision, Inc., Redmond, WA (US)

( * ) Notice: Subject to any disclaimer, the term of this patent is extended or adjusted under 35 U.S.C. 154(b) by 179 days.

(21) Appl. No.: 11/634,322

(22) Filed: Dec. 4, 2006

(65) Prior Publication Data

US 2007/0244357 A1    Oct. 18, 2007

(51) Int. Cl.
*A61B 1/06* (2006.01)
(52) U.S. Cl. .................. 600/160; 600/113; 600/478
(58) Field of Classification Search .......... 600/160, 600/109, 113, 173, 476–478
See application file for complete search history.

(56) References Cited

U.S. PATENT DOCUMENTS

| | | | | |
|---|---|---|---|---|
| 5,129,897 A | * | 7/1992 | Daikuzono | .......... 606/16 |
| 5,611,017 A | * | 3/1997 | Lee et al. | .......... 385/114 |
| 6,066,090 A | * | 5/2000 | Yoon | .......... 600/113 |
| 6,370,422 B1 | * | 4/2002 | Richards-Kortum et al. | 600/478 |
| 6,485,413 B1 | * | 11/2002 | Boppart et al. | .......... 600/160 |
| 6,564,087 B1 | * | 5/2003 | Pitris et al. | .......... 600/478 |
| 6,975,898 B2 | * | 12/2005 | Seibel | .......... 600/473 |
| 2005/0038322 A1 | * | 2/2005 | Banik | .......... 600/129 |
| 2006/0149134 A1 | * | 7/2006 | Soper et al. | .......... 600/182 |

\* cited by examiner

*Primary Examiner*—John P Leubecker
(74) *Attorney, Agent, or Firm*—Kevin D. Wills (57) ABSTRACT

Apparatuses and methods for scanned beam imagers and scanned beam endoscopes that utilize multiple light collectors are disclosed. In one aspect, a scanned beam imager is disclosed. The scanned beam imager includes a scanned beam source operable to scan a beam onto a region of interest of an object. The scanned beam imager further includes a first light collector structured to collect light reflected from the region of interest and a second light collector positionable relative to the scanning tip. The second light collector structured to collect light transmitted through the region of interest.

18 Claims, 9 Drawing Sheets

SCANNED BEAM IMAGERS AND ENDOSCOPES UTILIZING MULTIPLE LIGHT COLLECTORS

TECHNICAL FIELD

This invention relates to scanned beam systems and, more particularly, to scanned beam imagers and endoscopes.

BACKGROUND

Video endoscopes have been in general use since the 1980s for viewing the inside of the human body. Endoscopes are typically flexible or rigid devices that have an endoscope tip including an imaging unit, such as a digital camera or a scanned beam imager, configured for collecting light and converting the light to an electronic signal. The electronic signal is sent up a flexible tube to a console for display and viewing by a medical professional such as a doctor or nurse.

To improve performance, specialized endoscopes have been developed to best accomplish their intended function. For example, upper endoscopes are used for examination of the esophagus, stomach and duodenum, colonoscopes are used for examining the colon, angioscopes are used for examining blood vessels, bronchoscopes are used for examining the bronchi, laparoscopes are used for examining the peritoneal cavity, and arthroscopes are used for examining joint spaces. Instruments to examine the rectum and sigmoid colon, known as flexible sigmoidoscopes, have also been developed. The discussion of endoscopes herein generally applies to these and other types of endoscopes, and the term "endoscope" as used herein encompasses all these and other such devices.

Figure 1:
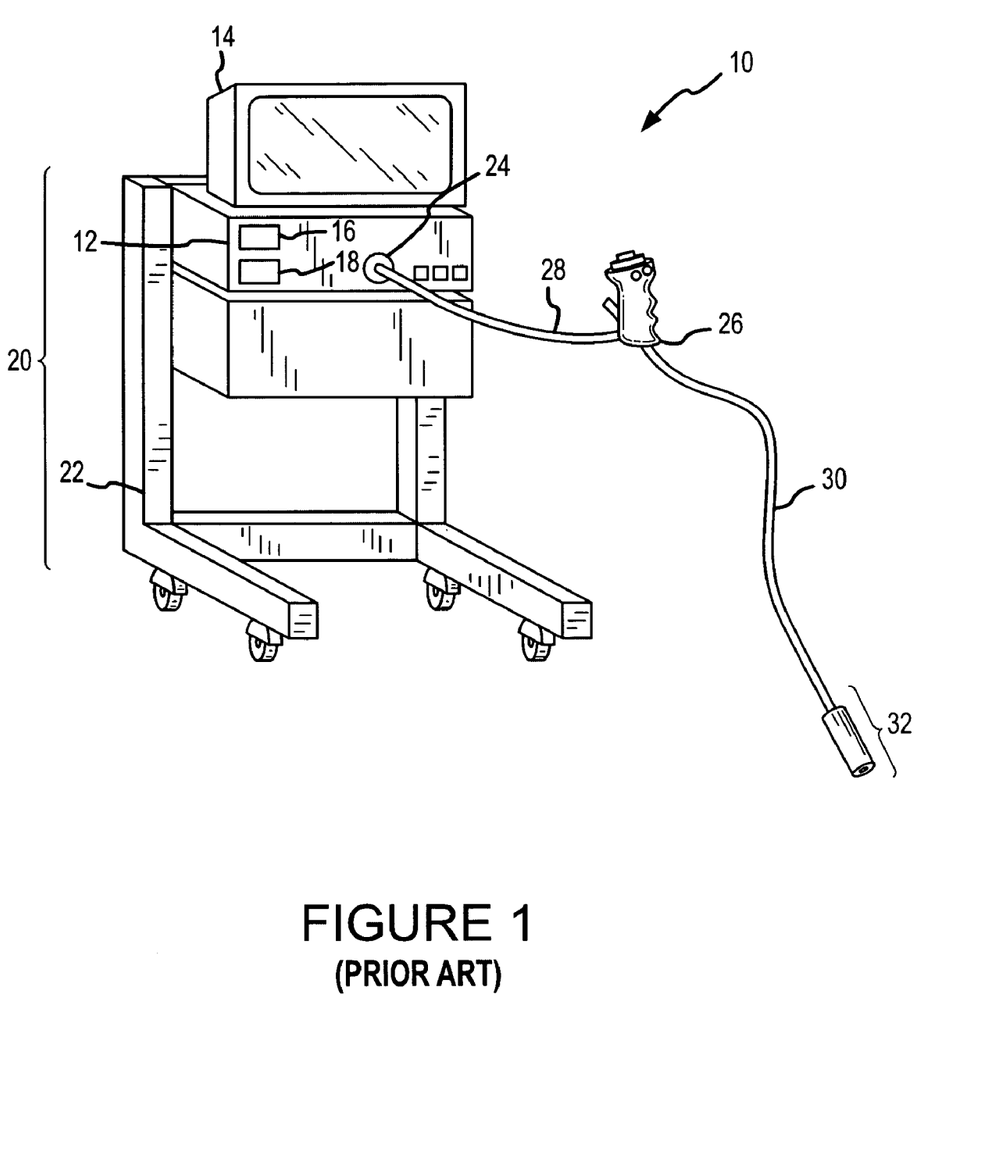
FIG. 1 is schematic illustration of a scanned beam endoscope according to the prior art.

Scanned beam endoscopes are a fairly recent innovation, and an example of a scanned beam endoscope is disclosed in U.S. patent application Ser. No. 10/873,540 ("'540 application") entitled SCANNING ENDOSCOPE, hereby incorporated by reference. FIG. 1 show a scanned beam endoscope 10 disclosed in the '540 application. The scanned beam endoscope includes a control module and monitor, all of which may be mounted on a cart 22, and collectively referred to as console 20. The scanned beam endoscope further includes an endoscope tip 30 having a scanning tip 32 with a scanning module configured to scan a beam across a field-of-view (FOV) and detection optical fibers (not shown) that collect reflected light from the FOV and transmit the signals, either as optical signals or electrical signals if converted using an optical-to-electrical converter at the scanning tip 32, to the console 20 for further processing.

The control module includes a scanning tip controller 16 for controlling the scanning of the beam from scanning tip 32 and an image processor 18 that processes image data signals received from the scanning tip 32 characteristic of the FOV. The console 20 communicates with a handpiece 26 through an external cable 28, which is connected to the console 20 via connector 24. The handpiece 26 is operably coupled to the endoscope tip 30 and allows the user to manipulate the position and image collection functions of the endoscope tip 30.

The endoscope tip 30 and scanning tip 32 thereof are configured for insertion into a body cavity for imaging internal surfaces thereof. In operation, the scanning tip 32 scans a beam of light over a FOV, collects the reflected light from the interior of the body cavity with the detection optical fibers (not shown), and sends image data signals representative of an image of the internal surfaces to the image processor 18 for image processing. A video image of the FOV is generated by the image processor 18 according to the time-sequential pattern through which the beam of light is scanned. The image generated by the image processor 18 is displayed on the monitor 14 for evaluation by a medical professional. While the scanned beam endoscope is an effective endoscope, the detection optical fibers (not shown) of the scanning tip 32 can only be used to collect reflected light from the FOV, which consequently limits the information about the tissue or organ being examined.

SUMMARY

Apparatuses and methods for scanned beam imagers and scanned beam endoscopes that utilize multiple light collectors are disclosed. In one aspect, a scanned beam imager is disclosed. The scanned beam imager includes a scanned beam source operable to scan a beam onto a region of interest of an object. The scanned beam imager further includes a first light collector structured to collect light reflected from the region of interest and a second light collector positionable relative to the scanning tip. The second light collector is structured to collect light transmitted through the region of interest.

In another aspect, a method of capturing an image of a region of interest of an object having a first side and an opposing second side is disclosed. A scanned beam source is provided. A first light collector is positioned to receive light reflected from the first side of the object. A second light collector is positioned to receive light transmitted through the region of interest and the second side of the object. A beam is scanned onto the first side of the object within the region of interest. At least a portion of the light reflected from the first side is collected with the first light collector. At least a portion of the light transmitted through the region of interest and the second side is collected with the second light collector. The image, which is characteristic of the region of interest, is generated based upon the collected light.

In another aspect, a scanned beam endoscope is disclosed. The scanned beam endoscope includes a scanning tip operable to scan a beam onto a region of interest of an object. The scanned beam endoscope further includes a first light collector structured to collect light reflected from the region of interest and a second light collector positionable relative to the scanning tip. The second light collector is structured to collect light transmitted through the region of interest.

In yet another aspect, a method of performing endoscopy with a scanned beam endoscope is disclosed. A scanning tip of the scanned beam endoscope is introduced into a body cavity. A first light collector may be positioned inside the body cavity. A second light collector may be positioned external to the body cavity. A beam emitted from the scanning tip is scanned onto a region of interest within the body cavity. At least a portion of light reflected by the region of interest is collected with the first light collector and at least a portion of light transmitted through the region of interest is collected with the second light collector.

DETAILED DESCRIPTION OF THE EMBODIMENTS

Apparatuses and methods for scanned beam imagers and scanned beam endoscopes that utilize multiple light collectors are disclosed. Many specific details of certain embodiments are set forth in the following description and in the figures in order to provide a thorough understanding of such embodiments. One skilled in the art, however, will understand that there may be additional embodiments, or that the disclosed embodiments may be practiced without several of the details described in the following description. In the figures and description that follow, like elements and features are identified by like or similar reference numerals.

Figure 2:
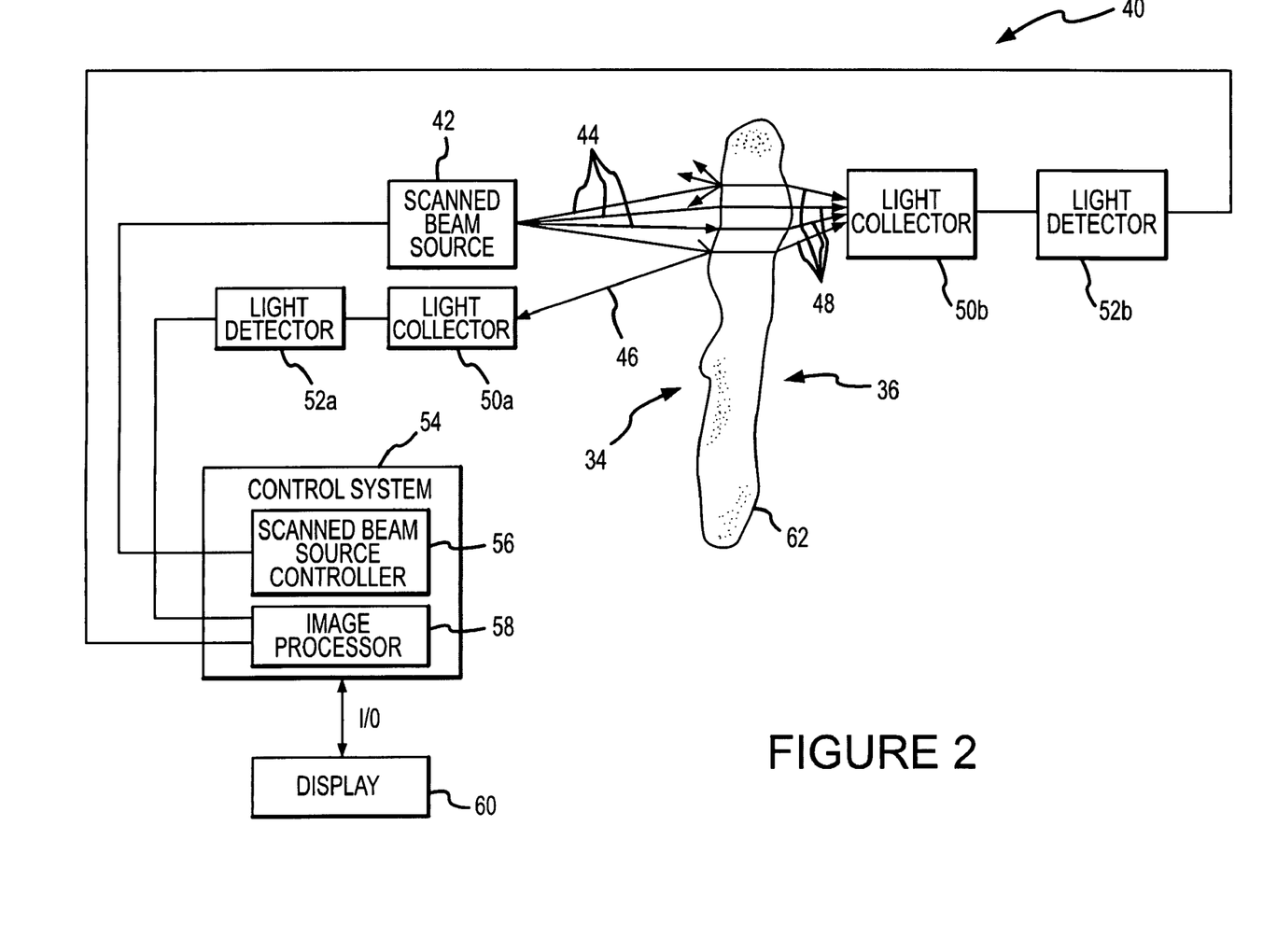
FIG. 2 is a functional block diagram of a scanned beam imager that includes a first light collector for collecting light reflected from a region of interest of an object and a second light collector for collecting light transmitted through the region of interest in accordance with one embodiment.

FIG. 2 is a functional block diagram of one embodiment of a scanned beam imager 40 operable to receive image information from both reflected and transmitted light. Accordingly, the scanned beam imager 40 is capable of discerning between pigmentation and transmissivity of a region of interest in a FOV, subsurface features in the region of interest such as an inclusion, regions of substantially thinner wall thickness, or other physical or optical features that affects the transmissivity of light through the region of interest. The scanned beam imager 40 includes a scanned beam source 42 operable to scan a beam 44 across a FOV onto a region of interest of an object 62 having a first side 34 and an opposing second side 36. The scanned beam source 42 may include a micro-electro-mechanical (MEMS) scanner operable to scan a beam across the FOV, an optical fiber that is moved in a selected scan pattern using an actuator, or another suitable scanned beam source. Additionally, the scanned beam source 42 may be configured to scan a beam having a selected polarization.

The scanned beam imager 40 further includes a light collector 50a that may be positioned independent from the scanned beam source 42 and configured for collecting light reflected by the region of interest on the object 62. A light detector 52a, such as one or more photodiodes, is optically coupled to the light collector 50a so that the reflected light collected by the light collector 50a may be received by the light detector 52 and converted to electrical image data signals. The scanned beam imager 40 further includes another light collector 50b that may be positioned independent from the scanned beam source 42 and configured for collecting light transmitted through the region of interest and the second side 36 of the object 62. A light detector 52b is optically coupled to the light collector 50b so that the transmitted light collected by the light collector 50b may be received by the light detector 52b. The light collectors 50a and 50b may be lenses, optical fibers or optical fiber bundles or another suitable structure configured for guiding, focusing, and/or collimating the reflected light 46 and the transmitted light 48.

While the scanned beam 44 illuminates pixels on the first side 34 of the object 62, a portion of the illuminating scanned beam 44 is reflected (e.g., specular reflected light and diffuse reflected light also referred to as scattered light) according to the properties of the object 62 at the pixels to produce reflected light 46. A portion of the scanned beam 44 scanned across the region of interest may also be transmitted through the second side 36 of the object 62, represented as transmitted light 48, and collected by the light collector 50b.

A control system 54 is coupled to the scanned beam source 42 and the light detectors 50a and 50b. The control system 54 includes a scanned beam source controller 56 coupled to the scanned beam source 42 and configured for controlling the scanning of the beam 44 of the scanned beam source 42. The control system 54 further includes an image processor 58 coupled to the light detectors 52a and 52b. The image processor 58 receives electrical image data signals from the light detectors 52a and 52b corresponding to the timing and intensity of the reflected light 46 and transmitted light 48 received by the respective light collectors 50a and 50b. The image processor 58 generates a digital representation of the region of interest based upon the electrical image data signals and transmits them for display on display 60 and/or further processing, decoding, archiving, printing, or other treatment or use via interface 56. The image of the region of interest may be generated by the image processor 58 by correlating the electrical image data signals received from the light detectors 52a and 52b with the time at which particular pixels on the region of interest of the object 62 are scanned with the beam 44 and the position of the pixels in the particular scan pattern.

Although discrete light detectors 52 and light collectors 50 are shown in FIG. 2, the light collectors 50 may be omitted. In such an embodiment, the light detectors 52a and 52b, such as PIN photodiodes or another type of electrical-optical converter, function to collect and convert the received light into electrical image data signals.

In some embodiments, an amplifier (not shown) may be coupled to the light detectors 52a and 52b to amplify the electrical image data signals before transmitting them to the image processor 58. The amplifier may be a trans-impedance amplifier (TIA) or another suitable amplifier. In some embodiments, an amplifier and/or light detector may be physically integrated with each of the light collectors 50a and 50b.

The scanned beam imager 40 may collect image information from both reflected and transmitted light. Accordingly, the scanned beam imager 40 is capable of discerning if a particular pixel on the first side 34 of the object 62 is dark because it is pigmented dark (i.e., absorbs the beam 44) or because the particular pixel on the first side 34 is more transmissive to the energy of the scanned beam 44 than a neighboring pixel. For example, a particular pixel may appear dark because the scanned beam 44 is not substantially reflected due to the portion of the region of interest on the object 62 substantially absorbing the scanned beam 44, while another pixel may appear dark because the particular pixel on the region of interest is substantially transmissive to the scanned beam 44. If the particular pixel on the region of interest is substantially transmissive, the transmitted light 48 through the region of interest will be collected by the light collector 50*b* and detected by the light detector 52*b*. Thus, the scanned beam imager 40's capability to detect light transmitted through the region of interest enables being able to discern whether particular pixels absorb the scanned beam 44 or transmit at least a portion of the scanned beam 44.

The information associated with the light transmitted through the region of interest being imaged (i.e., the light 48 in FIG. 2) may be displayed in a variety of different ways to alert the person viewing the image that there may be a difference in the physical and/or optical properties of a particular section of the region of interest. In one embodiment, the section of the region of interest being imaged that allows light to be transmitted therethrough may be indicated on the monitor 60. In various embodiments, an image generated by the image processor 58 includes an indication such as a red boundary defining the section of the region of interest that transmits a significant amount of light, a circle enclosing the section of the region of interest that transmits a significant amount of light, or another suitable indication that alerts the viewer. In another embodiment, the section of the region of interest that transmits a significant amount of light may be displayed on the monitor 60 by showing the section as bright in one image frame and significantly darker in another image frame.

In another embodiment, the light detectors 52*a* and 52*b* may be sensitive to the polarization of the light received from the light collectors 50*a* and 50*b*. In such an embodiment, the beam 44 scanned by scanned beam source 42 has a selected polarization. Since the light detectors 52*a* and 52*b* are sensitive to the polarization, the detectors 52*a* and 52*b* can determine whether the light collected by the light collectors 50*a* and 50*b* is the reflected light 46 from the first side 34 or the transmitted light 48 transmitted through the second side 36.

Figure 3:
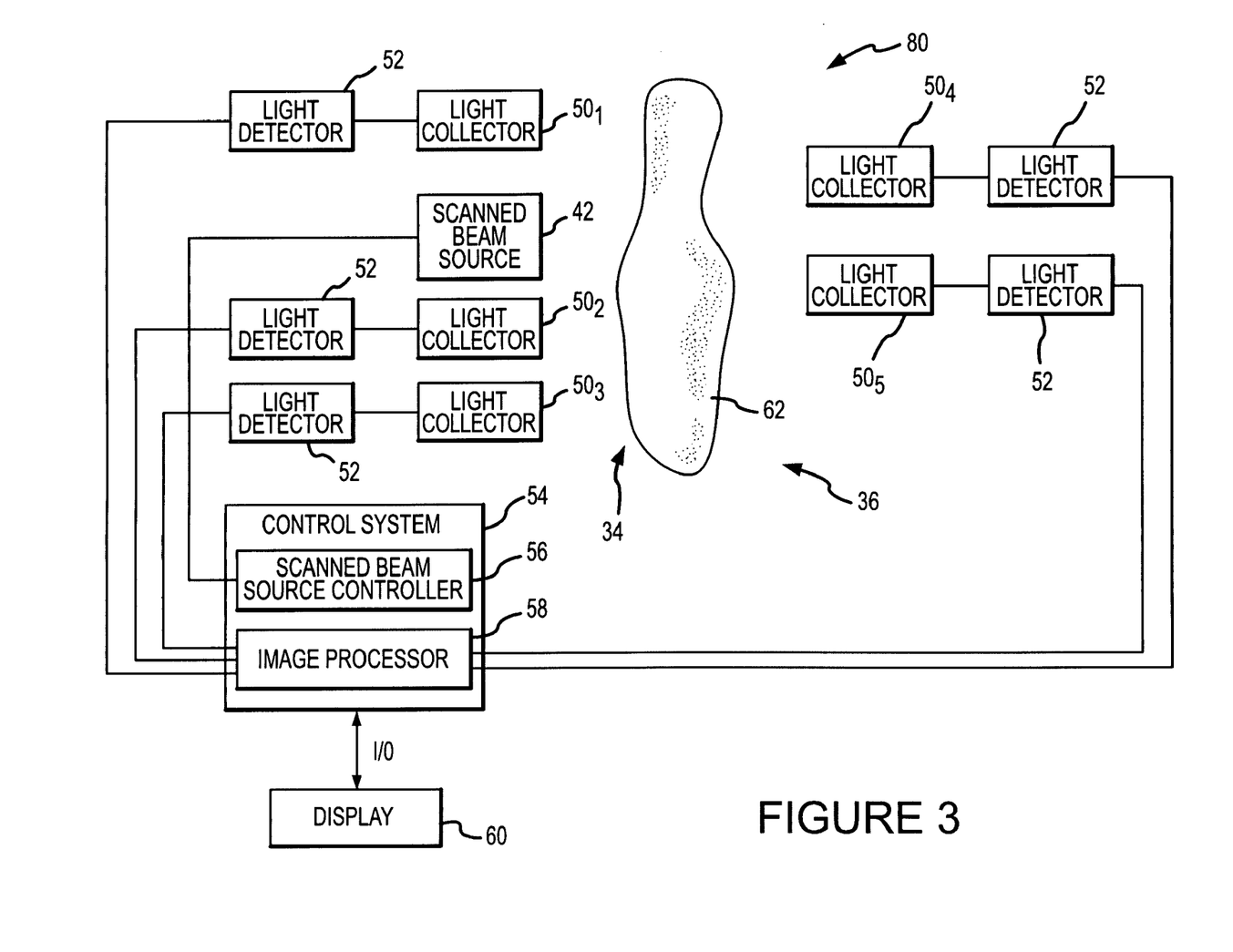
FIG. 3 is a functional block diagram of a scanned beam imager that includes multiple light collectors for collecting light reflected from a region of interest of an object and collecting light transmitted through the region of interest wherein each of the light collectors has a corresponding light detector in accordance with another embodiment.

FIG. 3 is a functional block diagram of a scanned beam imager 80 in accordance with another embodiment. The scanned beam imager 80 has many of the same components that are included in the scanned beam imager 40 of FIG. 2. Therefore, in the interest of brevity, the components of the two scanned beam imagers 40 and 80 that correspond to each other have been provided with the same or similar reference numerals, and an explanation of their structure and operation will not be repeated. In the scanned beam imager 80, each of the light collectors 50 are coupled to one of the light detectors 52. In operation, one of the light collectors $50_1$-$50_5$ may receive a relatively weak optical signal from a particular pixel on the region of interest, while another one of the light collectors $50_1$-$50_5$ may receive a relatively strong optical signal from the same pixel on the region of interest. Thus, the use of multiple light collectors $50_1$-$50_5$ diversifies the collection sources in case the position of one of the light collectors $50_1$-$50_5$ results in receiving a weak or nonexistent optical signal. It should be emphasized that the number of light collectors $50_1$-$50_5$ may be varied from the number shown in FIG. 3. Additionally, as with the scanned beam imager 40, each of the light collectors $50_1$-$50_5$ may be independently positionable from the scanned beam source 42.

In the scanned beam imager 80, the image processor 58 may compare the electrical image data signals received from each of the light detectors 52 on the first side 34 of the region of interest that receives reflected light and average the image data signals or selectively weight particular image data signals. For example, in one embodiment, the image processor 58 may discard a particularly strong reflective signal from the region of interest. In another embodiment, the image processor 58 may combine the electrical image data signals from the light detectors 52 on the first side 34 of the object 62 and combine the electrical image data signals on the second side 36 of the object 62. Additionally, the image processor 58 may perform the same type of signals processing to the image data signals transmitted from the light detectors 52 that receive light transmitted through the region of interest to the light collectors 50.

Figure 4:
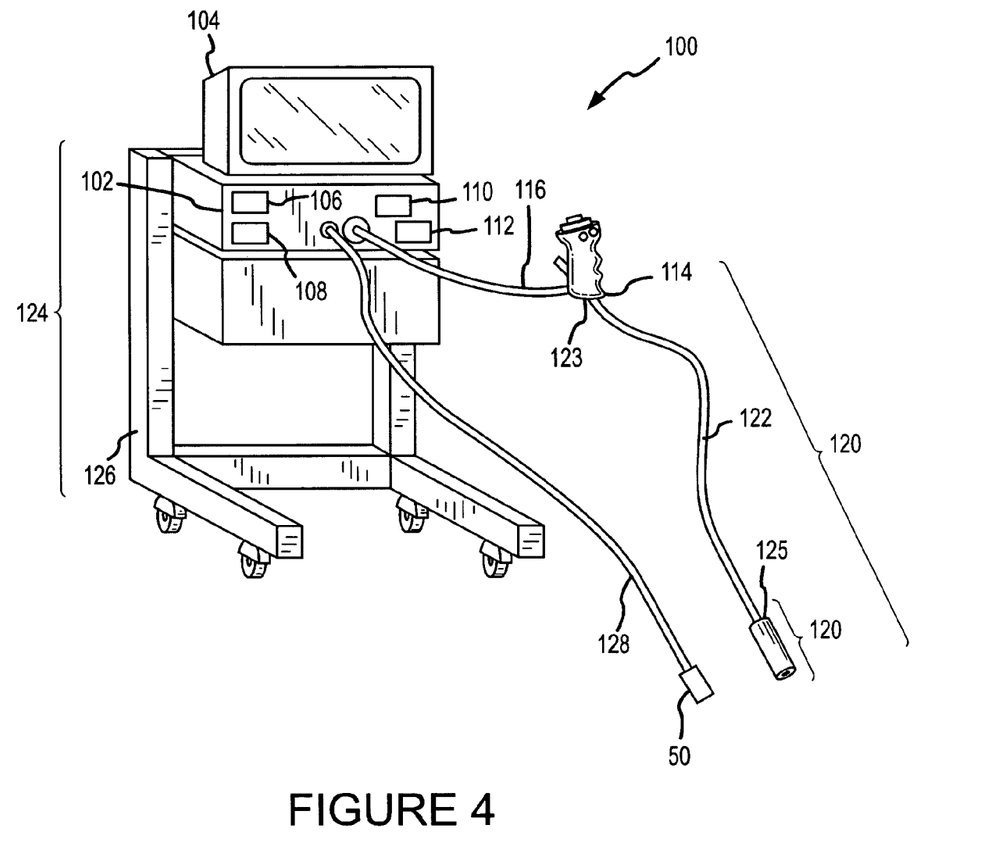
FIG. 4 is a schematic illustration of a scanned beam endoscope incorporating the teachings of the scanned beam imagers of FIGS. 2 and 3A-3B in accordance with one embodiment.
Figure 5:
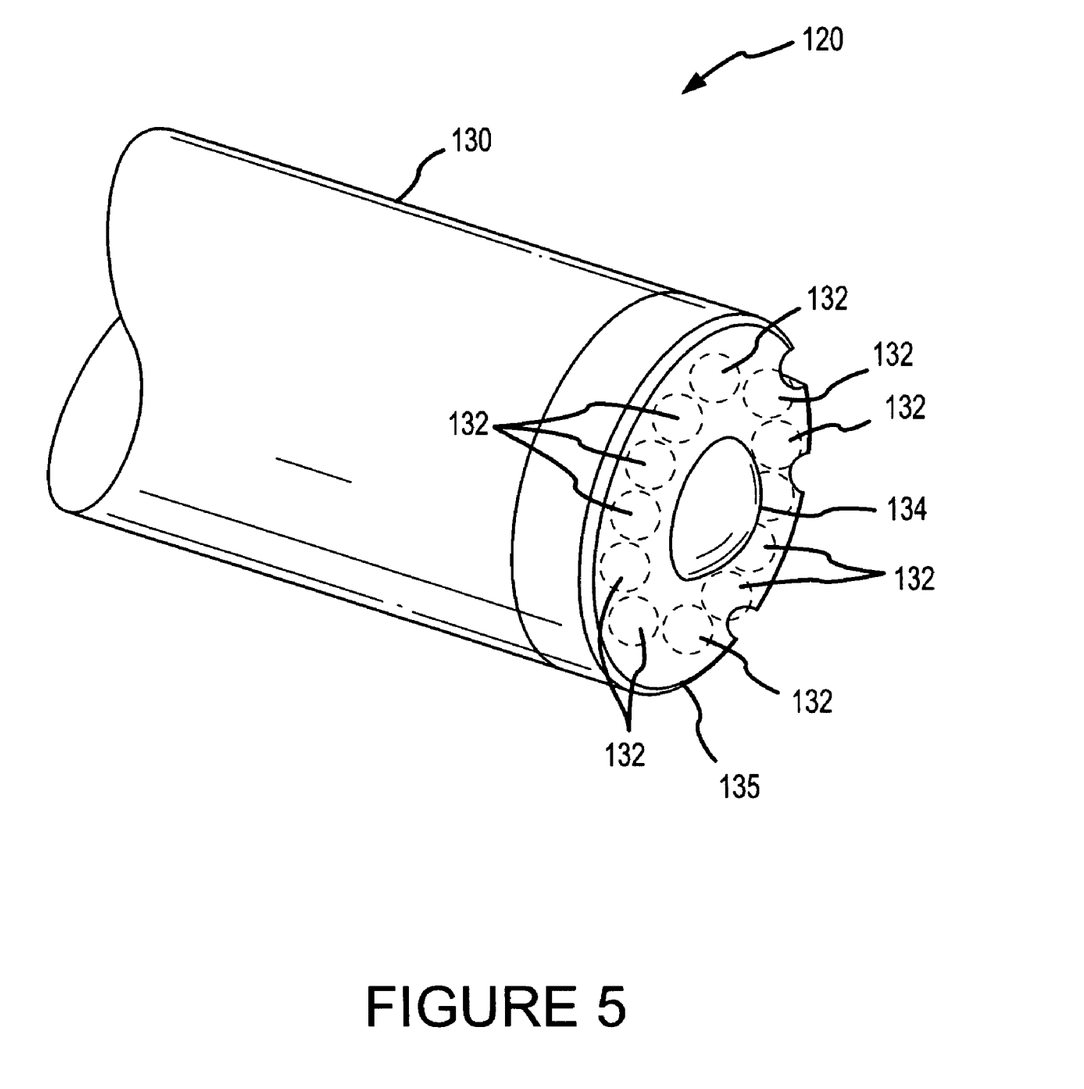
FIG. 5 is a schematic partial isometric view of the scanning tip shown in FIG. 4.
Figure 6:
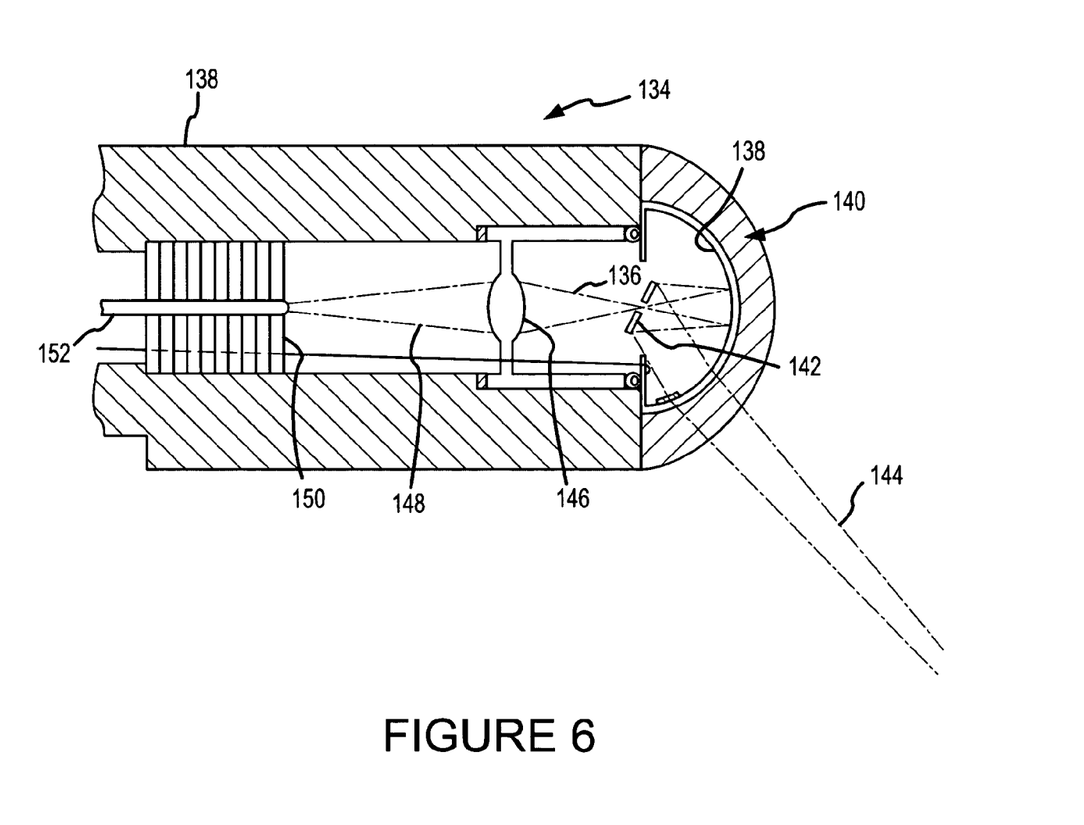
FIG. 6 is a schematic partial side cross-sectional view of the scanning module of FIG. 5.

The teachings of the scanned beam imagers 40 and 80 may be implemented in a scanned beam endoscope. FIGS. 4 through 6 illustrate a scanned beam endoscope 100 in accordance with one embodiment that incorporates such teachings. As shown in FIG. 4, the scanned beam endoscope 100 includes a control module 102 and monitor 104, all of which may be mounted on a cart 126, and collectively referred to as console 124. The control module 102 includes a controller 106 for controlling the operation of a scanning tip 120, an image processor 108 for processing image data signals associated with light reflected from and/or transmitted through the region of interest being imaged, a light source 110 coupled to the controller 106, and a light detector module 112. A handpiece 114 is operably coupled to the control module 102 through an external cable 116 to enable the user to manipulate the position and image collection functions of an endoscope tip 118.

The endoscope tip 118 includes a scanning tip 120 and a hollow, elongated body 122 having a proximal end 123 attached to the handpiece 114 and a distal end 125 attached to the scanning tip 120. The hollow, elongated body 122 encloses optical and electrical components, such as optical fibers and electrical wires, associated with the scanning tip 120. Depending upon the endoscope application, the elongated body 122 may be flexible or rigid. The scanning tip 120 includes a scanning module 134 (FIGS. 5 and 6) configured to scan a beam across a FOV, and a plurality of detection optical fibers 132 (FIG. 5) that collect light reflected from a region of interest in the FOV and transmit optical signals to the light detection module 112.

The scanned beam endoscope 100 further includes one or more light collectors 50 independently positionable relative to the scanning tip 120 that are optically coupled to the light detector module 112 via one or more optical fibers that are enclosed by an elongated hollow body 128. The light detector module 112 is operable to convert the optical signals received from the scanning tip 120 and the light collector 50 to electrical image data signals and transmit the electrical image data signals to the image processor 108. As with the aforementioned scanned beam imager embodiments, the light detector module 112 may include one or more photodiodes for converting the light received from the region of interest to electrical image data signals. Although the light detector module 112 is shown located in the control module 102, in another embodiment, one or more photodiodes may be physically integrated with the light collector 50 and electrical image data signals converted thereby may be transmitted to the image processor 108 for processing via electrical wires instead of optical fibers. In some embodiments, an amplifier, such as a TIA, may also be physically integrated with the light collector 50 or located in the control module 102 for amplifying the electrical image data signals before transmission to the image processor 108.

FIGS. 5 and 6 illustrate the scanning tip 120 and a scanning module 134 of the scanning tip 120, respectively, in more detail. Referring to FIG. 5, the scanning tip 120 includes a housing 130 that encloses and carries the scanning module 134, the detection optical fibers 132, and an end cap 135 affixed to the end of the housing 130. The detection optical fibers 132 may be disposed peripherally about the scanning module 134 within the housing 130 and transmit reflected light received from the region of interest to the light detector module 112. Referring to FIG. 6, the scanning module 134 has a housing 138 that encloses and supports a MEMS scanner 142 and associated components, an illumination optical fiber 152 affixed to the housing 138 by a ferrule 150 and coupled to the light source 110, and a beam shaping optical element 146. A dome 140 is affixed to the end of the housing 130 and may be hermetically sealed thereto in order to protect the sensitive components of the scanning module 134. In some embodiments, the light source 110 may output polarized light and the dome 140 may be structured to only transmit the scanned beam 144 when it exhibits a selected polarization.

In the embodiment of the scanning tip 120, the detection optical fibers 132 or other collection optics may be used to collect light received from the FOV. However, in other embodiments, the detection optical fibers 132, the light collector 50, or both may be omitted and, instead, a light detector such as PIN photodiodes or another type of electrical-optical converter that functions to collect and convert the received light into electrical image data signals and transmit such signals to the image processor 108 of the control module 102 may be used.

In operation, the scanning tip 120 is inserted into a body cavity to image a region of interest of an organ or tissue. The light collector 50 is positioned on or near the exterior of the wall that defines the body cavity. The illumination optical fiber 152 receives light from the light source 110 and outputs a beam 148 that is shaped by the beam shaping optical element 146 to form a shaped beam 136 having a selected beam shape. The shaped beam 136 may be transmitted through an aperture in the center of the MEMS scanner 142 or another opening in the MEMS scanner 142, reflected off a first reflecting surface 138 of the interior of the dome to the front of the scanner 142, and then reflected off of the scanner 142 as a scanned beam 144 through the dome 140. The scanned beam 144 is scanned across a FOV and reflected off a region of interest of the body cavity. At least a portion of the reflected light (e.g., specular reflected light and diffuse reflected light also referred to as scattered light) is collected by the detection optical fibers 132 of the scanning tip 120, transmitted to the light detection module 112, and subsequently transmitted to the image processor 108. The independently positionable light collector 50 also collects light transmitted through the region of interest and transmits either optical or electrical signals to the image processor 108 depending upon the particular configuration of the light collector 50 being used. The image processor 108 processes the image signals received from the scanning tip 120 and light collector 50 to generate an image characteristic of the region of interest being imaged.

The scanned beam endoscope 100 is depicted in FIG. 4 with only one light collector 50. In another embodiment shown in FIG. 7, a scanned beam endoscope 160 includes a plurality of light collectors 50 that may be positioned independently from a scanning tip 162. Unlike the scanning tip 120 of FIGS. 4 and 5, the scanning tip 162 may contain only the scanning module 134 and other related components such as an outer sheath covering the scanning module 134 and, thus, lacks the light collection capability of the scanning tip 120. In one embodiment, each of the light collectors 50 may be coupled to a light detector in a manner similar to the scanned beam imager 80 shown in FIG. 3. In other embodiments, the scanning tip 120 with integrated light collection functionality may be used in combination with multiple light collectors 50 for detecting reflected light from the region of interest and, additional light collectors 50 may be used to collect transmitted light through the region of interest. If multiple light collectors and light detectors are used, the image processor 108 may compare electrical image data signals in a manner similar to the scanned beam imager 80.

Figure 8:
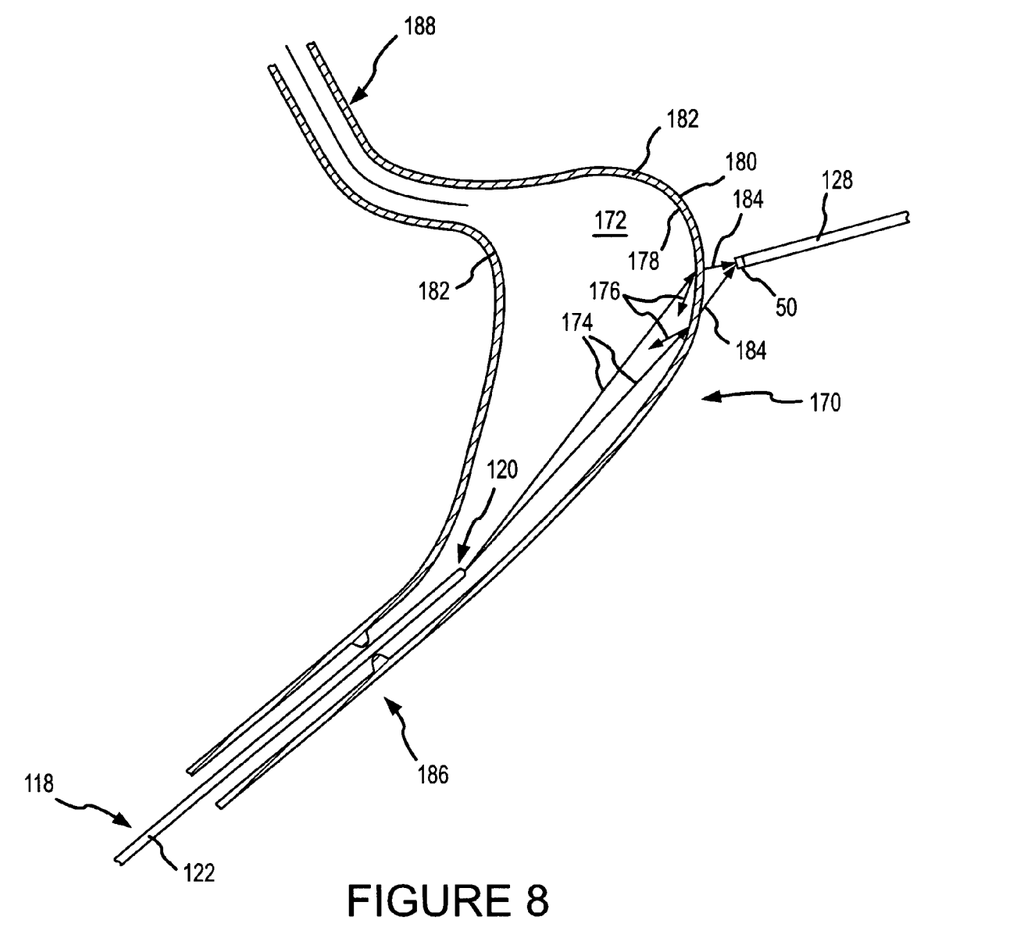
FIG. 8 is a schematic cross-sectional view illustrating the scanned beam endoscope of FIG. 4 being used to image a region of interest of a body cavity in accordance with one embodiment.

FIG. 8 shows a schematic illustration of a method of using the scanned beam endoscope 100 in accordance with one embodiment. The method described with reference to FIG. 8 shows using the scanned beam endoscope 100 for imaging a human stomach 170 having an esophagus 186 at one end and an small intestine 188 at the other end. However, the method may also be used for imaging any body cavity or wall of an organ or other tissue. The scanning tip 120 may be inserted through the esophagus 186 into the stomach 170 having a stomach cavity 172 defined by a stomach wall 182 with an interior surface 178 and an exterior surface 180. The light collector 50 may also be positioned in the space surrounding the stomach 170 on or near the exterior surface 180 of the stomach wall 172. The scanning tip 120 scans a beam 174 onto the interior surface 178. The interior surface 178 of the stomach wall 172 may reflect a portion of the scanned beam 174, shown as reflected light 176, which is collected with the scanning tip 120. Some of the light from the scanned beam 174 may be transmitted through the stomach wall 172 and collected with the light collector 50 positioned on the exterior of the stomach 170.

The scanned beam endoscope 100 may be sensitive to physical abnormalities and different disease states based on the amount of light that is reflected and transmitted through the tissue being analyzed. For example, a fluid filled inclusion in the stomach wall 172 may be detected because it may allow more of the light from the scanned beam 174 to be transmitted than if the fluid filled inclusion was not present. Additionally, since the scanned beam endoscope 100 is configured to detect light transmitted through a region of interest in an organ or other tissue, the thickness of the tissue may be determined.

Figure 7:
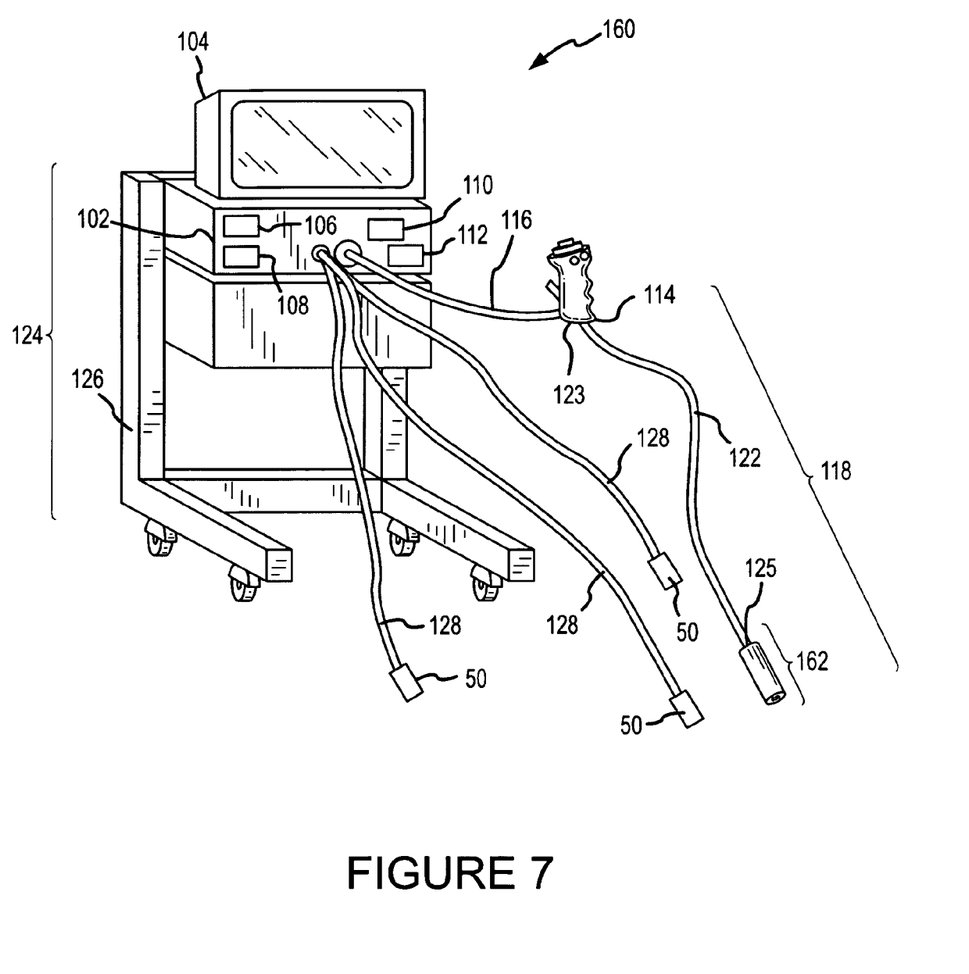
FIG. 7 is a schematic illustration of a scanned beam endoscope that utilizes a plurality of light collectors in accordance with yet another embodiment.

When the scanned beam endoscope 160 of FIG. 7 is used to examine, for example, the stomach 170 shown in FIG. 8, one more of the light collectors 50 may be positioned inside the stomach cavity 172 to diversify the number of light collectors so that at least some of them receive light reflected from the interior surface 178 of the stomach 170 and one or more light collectors 50 may be positioned on or near the exterior surface 180 of the stomach 170 to diversity the number of light collectors for receiving light transmitted through the stomach wall 182.

Figure 9:
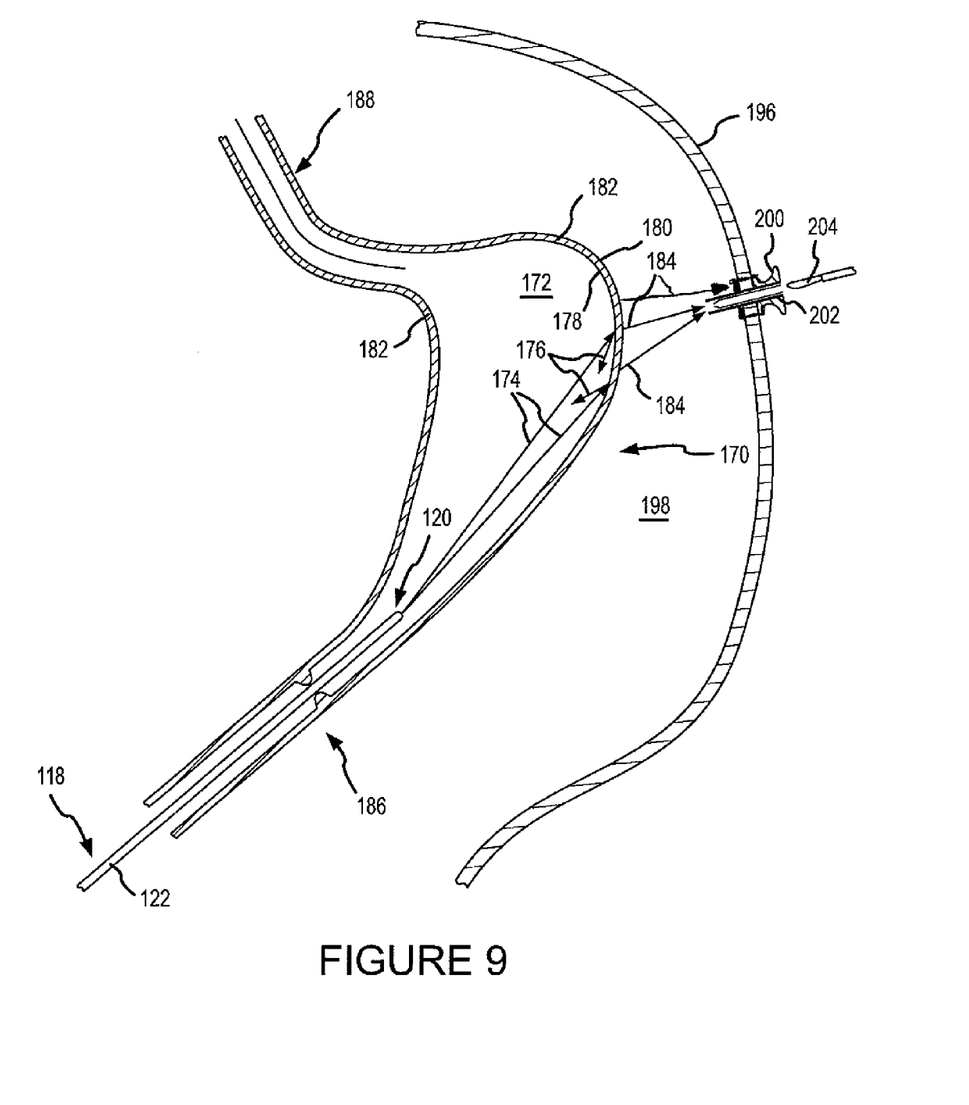
FIG. 9 is a schematic cross-sectional view illustrating the use of a trocar housing as a light collector in accordance with yet another embodiment.

In one embodiment, the light collectors 50 may each include a plurality of optical fibers that are positioned within a trocar housing or the trocar housing may be formed from a material at least partially transparent to the wavelength of the transmitted light 184 and thus function as a light collector. As known in the art, a trocar may include a trocar housing, a cannula assembly attached to the trocar housing and having a bore therein, and an obturator that slides through the bore to make an incision in a subject. With reference to FIG. 9, in one embodiment, a trocar housing 200 may be inserted into tissue 196 to gain access to the inside of a body cavity 198 surrounding a primary body cavity being imaged (e.g., the stomach cavity 178 of the stomach 170). Then, the surgical tools such as a scalpel 204 or forceps, or individual light collectors 50 may be inserted through the bore 202 in the trocar housing 200 while the trocar housing 200 is also used to collect the transmitted light 184. In some embodiments, the trocar housing 200 may be used to gain access to the primary body cavity, such as the stomach cavity 178, being imaged in order to collect the reflected light 176 in addition to or as an alternative to using one of the trocar housings 200 to gain access to the surrounding body cavity 198 to collect the transmitted light 184. Of course, the scanning tip 120 or 162, surgical tools, or individual light collectors 50 may be also inserted through the bore 202 of the trocar housing 200 to provide the scanned beam 174 and/or collect reflected light 176.

The information associated with the light transmitted through the tissue being examined (e.g., the light 184 in FIG. 8) may be displayed in a variety of different ways to alert the person analyzing the image that there may be a physical abnormality. In one embodiment, the section of the region of interest being imaged that allows light to be transmitted therethrough may be indicated on the monitor 104. In various embodiments, an image generated by the image processor 108 includes an indication such as a red boundary defining the section of the region of interest that transmits a significant amount of light, a circle enclosing the section of the region of interest that transmits a significant amount of light, or another suitable indication that alerts the viewer. In another embodiment, the section of the region of interest that transmits a significant amount of light on the monitor 104 may be displayed by showing the section as bright in one image frame and significantly darker in another image frame. Accordingly, the various embodiments for providing an indication to the viewer disclosed herein indicate to the viewer that a particular section of the region of interest has different optical and/or physical properties than the surrounding sections indicating that the tissue may be diseased, substantially thinner than the surround sections, have fluid filled inclusions, or combinations thereof.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of performing endoscopy with a scanned beam endoscope, comprising:
    introducing a scanning tip of the scanned beam endoscope into a body cavity;
    positioning a first light collector inside the body cavity;
    positioning a second light collector external to the body cavity;
    scanning a beam emitted from the scanning tip onto a region of interest within the body cavity;
    collecting at least a portion of light reflected by the region of interest with the first light collector; and
    collecting at least a portion of light transmitted through the region of interest with the second light collector.

2. The method of claim 1 wherein the scanning tip includes the first light collector and wherein the act of positioning a first light collector inside the body cavity comprises positioning the scanning tip within the body cavity.

3. The method of claim 1, further comprising generating an image based upon the reflected light collected by the first light collector and the transmitted light collected by the second light collector.

4. The method of claim 3 wherein the act of generating an image based upon the reflected light collected by the first light collector and the transmitted light collected by the second light collector comprises displaying the image including an indication of a region of high transmissivity of the beam within the region of interest.

5. The method of claim 1 wherein:
    the second light collector is configured as a trocar housing; and
    the act of positioning the second light collector external to the body cavity comprises inserting the trocar housing into tissue surround the body cavity.

6. The method of claim 1 wherein:
    the first light collector is configured as a trocar housing; and
    the act of positioning a first light collector inside the body cavity comprises inserting the trocar housing into a wall of the body cavity.

7. The method of claim 1 wherein the act of introducing a scanning tip of the scanned beam endoscope into a body cavity comprises inserting the scanning tip through a bore in the trocar housing.

8. The method of claim 1:
    wherein the first light collector comprises a plurality of first light collector elements each of which is structured to collect light reflected from the region of interest and to output first image data signals corresponding to the light reflected from the region of interest, and the second light collector comprises a plurality of second light collector elements each of which is structured to collect light reflected from the region of interest and to output first image data signals corresponding to the light transmitted through the region of interest; and
    further comprising comparing at least some of the first image data signals from the first light collector elements and comparing at least some of the second image data signals from the second light collector elements.

9. The method of claim 8 wherein the act of comparing at least some of the first image data signals from the first light collector elements and comparing at least some of the second image data signals from the second light collector elements comprises selectively weighting at least some of the first and second image data signals.

10. The method of claim 8 wherein the act of comparing at least some of the first image data signals from the first light collector elements and comparing at least some of the second image data signals from the second light collector elements comprises averaging at least some of the first and second image data signals.

11. The method of claim 1, further comprising detecting a disease state by evaluating the reflected and transmitted light.

12. The method of claim 1, further comprising detecting a discontinuity in a wall of the cavity by evaluating the reflected and transmitted light.

13. A method of capturing an image of a region of interest of an object having a first side and an opposing second side, comprising:
    providing a scanned beam source;
    positioning a first light collector to receive light reflected from the first side of the object;
    positioning a second light collector to receive light transmitted through the region of interest and the second side of the object;
    scanning a beam onto the first side of the object within the region of interest;
    collecting at least a portion of the light reflected from the first side with the first light collector;
    collecting at least a portion of the light transmitted through the region of interest and the second side with the second light collector; and
    generating the image, which is characteristic of the region of interest, based upon the collected light.

14. The method of claim 13 wherein the act of generating the image, which is characteristic of the region of interest, based upon the collected light comprises displaying the image including an indication of a region of high transmissivity of the beam within the region of interest.

15. The method of claim 13 wherein the first light collector comprises a plurality of first light collector elements commonly coupled to a first light detector and the second light collector comprises a plurality of second light collector elements commonly coupled to a second light detector.

16. The method of claim 13:
wherein the first light collector comprises a plurality of first light collector elements each of which is structured to collect light reflected from the region of interest and to output first image data signals corresponding to the light reflected from the region of interest, and the second light collector comprises a plurality of second light collector elements each of which is structured to collect light reflected from the region of interest and to output first image data signals corresponding to the light transmitted through the region of interest; and further comprising comparing at least some of the first image data signals from the first light collector elements and comparing at least some of the second image data signals from the second light collector elements.

17. The method of claim 16 wherein the act of comparing at least some of the first image data signals from the first light collector elements and comparing at least some of the second image data signals from the second light collector elements comprises weighting at least some of the first and second image data signals.

18. The method of claim 16 wherein the act of comparing at least some of the first image data signals from the first light collector elements and comparing at least some of the second image data signals from the second light collector elements comprises averaging at least some of the first and second image data signals.

* * * * *

UNITED STATES PATENT AND TRADEMARK OFFICE
CERTIFICATE OF CORRECTION

PATENT NO.         : 7,476,197 B2                                              Page 1 of 1
APPLICATION NO. : 11/634322
DATED              : January 13, 2009
INVENTOR(S)        : Christopher A Wiklof and Michael P Weir It is certified that error appears in the above-identified patent and that said Letters Patent is hereby corrected as shown below:

TITLE PAGE, item [73]
Add "Ethicon Endo-Surgery, Inc., Cincinnati, OH (US)" after "Microvision, Inc., Redmond, WA (US)" in the Assignee category.

Signed and Sealed this

Second Day of June, 2009

JOHN DOLL
*Acting Director of the United States Patent and Trademark Office*